United States Patent
Thompson et al.

(10) Patent No.: US 6,804,546 B1
(45) Date of Patent: Oct. 12, 2004

(54) MULTIPLE CONTRAST ECHO-PLANAR IMAGING FOR CONTRAST-ENHANCED IMAGING

(75) Inventors: Michael R. Thompson, Cleveland Heights, OH (US); Dee H. Wu, Shaker Heights, OH (US); Wayne R. Dannels, Richmond Heights, OH (US); Christopher K. Anand, Chesterland, OH (US)

(73) Assignee: Koninklijke Philips Electronics, N.V., Eindhoven (NL)

(*) Notice: Subject to any disclaimer, the term of this patent is extended or adjusted under 35 U.S.C. 154(b) by 352 days.

(21) Appl. No.: 09/885,884

(22) Filed: Jun. 20, 2001

Related U.S. Application Data

(60) Provisional application No. 60/285,543, filed on Apr. 20, 2001.

(51) Int. Cl.⁷ ............................. A61B 5/055; G01V 3/00
(52) U.S. Cl. ..................... 600/410; 600/420; 324/306; 324/309
(58) Field of Search ................................ 600/410, 419, 600/420; 324/306, 307, 309; 424/9.3

(56) References Cited

U.S. PATENT DOCUMENTS

| | | | | |
|---|---|---|---|---|
| 4,734,646 A | * | 3/1988 | Shenoy et al. | 324/309 |
| 5,168,226 A | * | 12/1992 | Hinks | 324/309 |
| 5,190,744 A | | 3/1993 | Rocklage et al. | 424/9 |
| 5,268,640 A | * | 12/1993 | Du et al. | 324/309 |
| 5,311,133 A | * | 5/1994 | Dannels | 324/309 |
| 5,327,088 A | * | 7/1994 | Pipe | 324/309 |
| 5,869,023 A | * | 2/1999 | Ericcson et al. | 424/9.36 |
| 6,075,362 A | * | 6/2000 | Loncar et al. | 324/309 |
| 6,104,943 A | * | 8/2000 | Frederick et al. | 600/410 |
| 6,127,826 A | | 10/2000 | Thompson et al. | 324/307 |
| 6,492,811 B1 | * | 12/2002 | Foxall | 324/309 |
| 6,583,623 B1 | * | 6/2003 | Kwok et al. | 324/307 |
| 6,650,925 B2 | * | 11/2003 | Wang | 600/410 |

OTHER PUBLICATIONS

Papanikolaou, et al. "Comparison of Dual Spin Echo Planar Imaging (SE_EPI), Turbo Spin Echo With Fat Suppression and Conventional Dual Spin Echo Sequences for $T_2$–weighted MR Imaging of Focal Liver Lesions", Magnetic Resonance Imaging 18 (2000) 715–719.

Uematsu, et al. "Vascular Permeability: Quantitative Measurement With Double–Echo Dynamic MR Imaging–Theory and Clinical Application", Radiology 2000; 214:912–917.

(List continued on next page.)

*Primary Examiner*—Shawna J. Shaw
(74) *Attorney, Agent, or Firm*—Fay, Sharpe, Fagan, Minnich & McKee, LLP

(57) ABSTRACT

A dose of a contrast agent (44) is administered to the patient (42). A magnetic resonance is excited by an RF pulse (200) in a region of interest of the patient (42). An echo-planar imaging (EPI) readout waveform is implemented a preselected duration after the excitation to generate $T_2$ or $T_2^*$ weighted data. During the preselected duration, another echo planar readout waveform is implemented to generate $T_1$ or proton density weighted data. The data is reconstructed (56) to generate a $T_2$ or $T_2^*$ weighted image and a $T_1$ weighted image. The $T_1$ and $T_2$ or $T_2^*$ weighted images are combined (62) to generate a contrast enhanced image.

19 Claims, 7 Drawing Sheets

OTHER PUBLICATIONS

Heiland, et al. "Simultaneous Assessment of Cerebral Hemodynamics and Contrast Agent Uptake in Lesions With Disrupted Blood–Brain Barrier", Magnetic Resonance Imaging, vol. 17, No. 1, pp 21–27 1999.

Miyati, et al., "Dual Dynamic Contrast–Enhanced MR Imaging", JMRI 1997; 7:230–235. 1996.

Chen, et al., "Mapping Drug–Induced Changes in Cerebral $R_2^*$ By Multiple Gradient Recalled Echo Functional MRI". Magnetic Resonance Imaging, vol. 14, No. 5, pp. 469–476, Börnert, et al., "Single–Shot–Double–Echo–EPI", Magnetic Resonance Imaging, vol. 12, No. 7, pp. 1033–1038, 1994.

Bandettini, et al., "Simultaneous Mapping of Activation–Induced $\Delta R2^*$ and $\Delta R2$ in the Human Brain Using a Combined Gradient–Echo and Spin–Echo EPI Pulse Sequence", Proceedings of the SMRM, vol. 1, Twelfth Annual Scientific Meeting, Aug. 14–20, 1993, NY, NY, p. 169.

Donahue, et al., "Utility of Acquiring Vascular Bloor Volume, Permeability and Morphology Information from Dynamic Susceptibility Contrast Agent Studies in Patients with Brain Tumors", ISMRM Philadelphia, PA 1999 (Abstract 149).

Donahue, et al., ". . . Angiogenesis Using Simultaneously-Acquired Gradient–Echo & Spin–Echo EPI During Dynamic Susceptibility Contrast" Proceedings of the ISMRM, Sydney, Australia Apr. 18–24, 1998, V. 3, p. 1640.

Donahue, et al., "Utility of Simultaneously Acquired Gradient–Echo and Spin–Echo Cerebral Blood Volume and Morphology Maps in Brain Tumor Patients", Magnetic Resonance in Medicine, vol. 43, Jun. 2000, pp 845–853.

* cited by examiner-

MULTIPLE CONTRAST ECHO-PLANAR IMAGING FOR CONTRAST-ENHANCED IMAGING

This application claims the benefit of U.S. Provisional Application No. 60/285,543, filed on Apr. 20, 2001.

BACKGROUND OF THE INVENTION

The present invention relates to the magnetic resonance arts. It finds particular application in medical diagnostic imaging and will be described with reference thereto. However, it will be appreciated that the invention will also find application in other types of imaging, spectroscopy, and the like.

A typical magnetic resonance (MR) imaging sequence includes an RF excitation pulse, e.g. a 90° pulse, with a corresponding slice- or slab-selective magnetic gradient pulse, followed by a series of spatial encoding and readout magnetic field gradient pulses. In some sequences a second 180° refocusing pulse is applied between the initial excitation pulse and the spatial encoding/readout region. The 180° pulse effectively reverses the dephasing effect of small spatial variations in the MR frequency due to spatial variations in the applied magnetic field, and refocuses the magnetization to form a spin-echo. MR imaging is performed using various imaging modes which usually vary with respect to the method and timing of the spatial encoding and data readout sequences.

The choice of spatial encoding and data readout scheme has significant consequences on the imaging contrast, resolution, and scanning speed. Two imaging parameters are the time-to-echo, $T_E$, and the repeat time between RF excitations, $T_R$. Sampling the induced resonance nearer to the excitation emphasizes proton density weighting or $T_1$ weighting in which the contrast strongly reflects the regrowth rate of the $M_Z$ component of the net magnetization. Sampling the magnetization later emphasizes $T_2$ weighting in which the contrast strongly reflects the decay rate of the $M_{XY}$ component of the net magnetization.

Proton density ($\rho$) weighting is obtained when the $T_E$ delay is short and the magnetic resonance has minimal time to decay, so that the density of resonant hydrogen protons is measured. $T_2^*$ weighting is obtained using a longer $T_E$ delay so that the fastest ($T_2^*$) magnetic resonance decay is a factor. The $T_2^*$ decay differs from $T_2$ in that $T_2^*$ includes inhomogeneous dephasing due to static magnetic field inhomogeneities. To measure the "pure" $T_2$ corresponding to dephasing due to molecular interactions (excluding inhomogeneous dephasing), a 180° RF refocusing pulse is applied to induce a spin-echo during the sampling interval. Other types of pre-pulses can also be applied to provide fat suppression, MTC, et cetera.

Prior spatial encoding and readout schemes have been configured to provide a variety of $\rho$, $T_2$, or $T_2^*$ weightings. The choice of spatial encoding scheme strongly affects the scan speed and resolution. A popular MR imaging mode is echo-planar imaging (EPI). In the EPI imaging mode, an oscillating read gradient generates a series of gradient echoes. Phase encoding pulses between echoes step the sampling through k-space in a back-and-forth rastering fashion. The speed of EPI is preferably sufficient that the k-space data for an entire planar (slice) image is obtained from a single RF magnetic resonance excitation, i.e. "single-shot" EPI, or SS-EPI. The rapidly switched gradients along with a rastered readout timing sequence of SS-EPI produce complete slice scans in as little as a few hundred milliseconds or less. This speed makes SS-EPI an ideal method for clinical imaging when short scan times are important. Reduced scan times translate to reduced image blurring due to patient movements, respiration, cardiac action, and the like.

The EPI technique encompasses a number of variants, including several techniques collectively known to the art as partial parallel imaging (PPI). In the PPI techniques, a phased array receive coil simultaneously measures the MR response using a plurality of phased receive coils and combines the data from the array to acquire a plurality of k-space samples in parallel.

Enhancement in MR imaging can also be obtained through the use of multiple image techniques. In these methods, the spatial encoding scheme is designed so that multiple images, typically using more than one image contrast mode, are obtained from the echo train following a single RF excitation pulse. For example, a $T_2^*$ weighted image and a $T_2$ weighted image can be obtained.

Another type of MR imaging is contrast-enhanced imaging. In this type of MR imaging, a magnetic contrast agent, such as a gadolinium chelate, is administered to the patient, such as by a bolus injection. The magnetic contrast agent provides enhanced MR contrast versus intrinsic imaging. In some studies, the preferential concentrating of the contrast agent in particular organs or tissues is imaged. In vascular imaging, the distribution of an administered contrast agent is monitored over time to study the performance of major blood vessels. Similarly, the perfusion of the contrast agent through tissues or organs enables study of the capillary performance in the targeted areas.

In order to quantitatively analyze perfusion by contrast-enhanced MR imaging, it is useful to quantify the concentration of the contrast agent in the imaged area based upon the MR image. In the exemplary case, the gadolinium chelate strongly reduces the $T_2$ weighted signal and $T_2^*$ weighted signal. In a $T_2$ weighted MR image, the areas of high gadolinium chelate concentration appear darker than the surrounding areas. In principle, therefore, the contrast agent concentration can be extracted from the percentage darkening or from similar quantitative image analysis. Unfortunately, competing effects, such as brightening due to $T_1$ shortening, can counteract the $T_2$ darkening effect of the gadolinium chelate and produce errors in the quantitative analysis.

The prior art also discloses taking a reference image prior to administration of the contrast agent. This approach has the disadvantage that the image of the contrast agent usually needs to be registered spatially with the reference image to correct for patient movement or other spatial shifting.

An effective method is needed for correcting these errors in quantitative contrast-enhanced perfusion imaging. Such correction would preferably utilize additional non-$T_2$ weighted images to account for extraneous, non-$T_2$ contrast mechanisms. However, the collection of these additional images is limited by the time constraints imposed by the dynamic perfusion process. The present invention contemplates a new imaging method which overcomes these limitations and others.

SUMMARY OF THE INVENTION

According to one aspect of the invention, a method of magnetic resonance imaging is disclosed. A magnetic resonance contrast agent is administered to a subject, which contrast agent alters $T_2$ and $T_2^*$ magnetic resonance characteristics. A magnetic resonance is excited in a region of interest of the subject which receives the contrast agent. A first echo planar image readout waveform is applied which generates first image data. After the first echo planar image readout waveform, a second echo planar image readout waveform is applied and a $T_2$ or $T_2^*$ weighted image data is generated. The image data is reconstructed to generate a proton density weighted or a $T_1$ weighted image representation and a $T_2$ or $T_2^*$ weighted image representation. The $T_2$ or $T_2^*$ weighted image representation is corrected with the first image representation.

Preferably, the method includes applying an RF inversion pulse between the first and second echo planar image readout waveforms.

The method preferably includes applying a third echo planar image readout waveform and generating the other of $T_2$ and $T_2^*$ weighted image data. Optionally, an RF inversion pulse is applied between the second and third echo planar image readout waveforms, such that the second echo planar image readout waveform generates $T_2^*$ weighted data and the third image readout waveform generates $T_2$ weighted data. The $T_2$ weighted data is preferably reconstructed into a $T_2$ weighted image representation, and the $T_2$ weighted image representation is preferably modified with the first image representation.

The method preferably includes reconstructing the $T_2$ or $T_2^*$ weighted image data and a portion of the first image data to generate the $T_2$ or $T_2^*$ weighted image representation, and reconstructing a portion of the $T_2$ or $T_2^*$ weighted image data and the first image data to generate the first image representation. Optionally, the portion of the $T_2$ or $T_2^*$ weighted data used in generating the first image and the portion of the first image data used in generating the $T_2$ or $T_2^*$ weighted image include interleaved data lines adjacent an edge of k-space. Optionally, additional data lines are generated by conjugate symmetry.

Preferably, the method includes repeating steps of the method a plurality of times to generate a series of first image representations and a series of $T_2$ or $T_2^*$ weighted image representations. These image series are preferably combined to generate a third series depicting a temporal evolution of the contrast agent in the region of interest.

Preferably, the method includes combining the first image representation and the $T_2$ or $T_2^*$ weighted image representation to generate a third image representation, and then repeating steps of the method a plurality of times to generate a series of third image representations depicting a temporal evolution of the contrast agent in the region of interest.

In the method, the contrast agent is preferably a gadolinium chelate.

At least one of the steps of generating the first image data and generating the second image data optionally advantageously includes generating image data using a partial parallel imaging technique.

According to another aspect of the invention, a method of contrast enhanced magnetic resonance imaging is disclosed. A subject is injected with a contrast agent, magnetic resonance is excited in a region of interest, the excited magnetic resonance is permitted to decay for a preselected duration to optimize one of $T_2$ and $T_2^*$ weighting, and after the preselected duration an echo planar image readout waveform is applied to generate $T_2$ or $T_2^*$ weighted data. The method further includes, during the preselected duration, applying another echo planar image readout waveform to generate $T_1$ weighted data.

According to yet another aspect of the invention, a method is disclosed for imaging a patient using a magnetic resonance (MR) imaging apparatus. The MR apparatus includes a patient support means, a main magnet, a slice-select gradient pulse generator, a phase-encode gradient pulse generator, a read gradient pulse generator, a plurality of RF coils, an RF transmitter, and a receiver. The method includes the steps of: administering a contrast agent to the patient; exciting a magnetic resonance in the patient using the RF transmitter and at least one of the plurality of RF coils in conjunction with the slice-select gradient generator; encoding and reading the magnetic resonance using the phase encode and the read gradient generators in conjunction with at least one of the plurality of RF coils and the receiver, the encoding and reading implementing a first echo-planar image readout waveform; encoding and reading the magnetic resonance using the phase encode and the read gradient generators in conjunction with at least one of the plurality of RF coils and the receiver, the encoding and reading implementing a second echo-planar image readout waveform; and reconstructing the read, encoded, magnetic resonance into first and second image representations.

Preferably, the method further includes comparing the first image representation with the second image representation to obtain a third image representation thereby. Optionally, the method includes repeating the steps of exciting a magnetic resonance, encoding, reading, and reconstructing first and second images, and comparing the first images with the second images to obtain third images thereby. A temporal evolution of at least one of the first, second, and third images is determined.

In the step of reconstructing the second image, a portion of the phase and frequency encoded resonance from the first echo planar image readout waveform is preferably reconstructed into the second image.

In the method, the first echo planar image sequence phase encoding preferably includes phase encoding a first portion of the resonance such that a $k_y$ component single-steps in a first direction, and phase encoding a second portion of the resonance such that the $k_y$ component double-steps in the first direction. The second echo planar image readout waveform phase encoding preferably includes phase encoding a first portion of the resonance such that the $k_y$ component double-steps opposite to the first direction, and phase encoding a second portion of the resonance such that the $k_y$ component single-steps opposite to the first direction. The reconstructing step preferably includes reconstructing the first and second portions of the first echo planar sequence and the first portion of the second echo planar sequence into the first image representation, and reconstructing the second portion of the first echo planar sequence and the first and second portions of the second echo planar sequence into the second image representation.

According to still yet another aspect of the invention, a magnetic resonance imaging apparatus is disclosed. A main magnet generates a temporally constant magnetic field through an examination region. An RF system excites and manipulates magnetic resonance in the examination region and receives and demodulates magnetic resonance signals from the examination region into data lines. A sorter is provided for sorting the data lines between a first data memory and a second data memory. A gradient magnetic field system generates magnetic field gradients across the examination region to spatially encode the resonance signals. A sequence controller: (i) controls the RF system to induce resonance; (ii) controls the RF and gradient systems to implement a first echo planar readout waveform which generates $T_1$ weighted data lines; (iii) controls the RF and gradient systems to implement a second echo planar readout waveform which generates one of $T_2$ and $T_2^*$ weighted data lines, and (iv) controls the sorter to sort the $T_1$ and $T_2$ or $T_2^*$ weighted data lines between the first and second data memories. A reconstruction processor reconstructs data lines from the first data memory into a first image representation and data lines form the second data memory into a second image representation.

The magnetic resonance apparatus preferably further includes a means for injecting a contrast agent into a subject in the examination region, and an image processor for combining the first and second image representations into a contrast agent enhanced image representation. Optionally, the sequence controller controls the sorter to sort all of the $T_1$ weighted data lines and a portion of the $T_2$ or $T_2^*$ weighted data lines into the first image memory, and all of the $T_2$ or $T_2^*$ weighted data lines and a portion of the $T_1$ weighted data lines into the second image memory.

Preferably, the RF system further includes a phased array receive coil, and a partial parallel imaging (PPI) integrator which processes the readout of the phased array receive coil to generate data lines. The PPI integrator preferably processes the readout of the phased array receive coil using one of a simultaneous acquisition of spatial harmonics (SMASH) technique, a sensitivity encoding (SENSE) technique, and a parallel imaging with localized sensitivities (PILS) technique.

One advantage of the present invention is that it facilitates correction of extraneous MR effects.

Another advantage of the present invention is that it facilitates faster scan times.

Another advantage of the present invention is that it provides multiple images with complementary dynamic range.

Another advantage of the present invention is that it facilitates quantitative contrast-enhanced imaging.

Another advantage of the present invention is that it corrects for extraneous image contrast in perfusion imaging.

Yet another advantage of the present invention is that it separates out counteracting MR effects in contrast enhanced $T_2$ weighted SS-EPI imaging.

Still yet another advantage of the present invention is that it provides additional MR data for a given imaging time that can be processed or combined to obtain improved and/or additional diagnostic information versus the prior art.

Still further advantages and benefits of the present invention will become apparent to those of ordinary skill in the art upon reading the following detailed description of the preferred embodiment.

BRIEF DESCRIPTION OF THE DRAWINGS

The invention may take form in various components and arrangements of components, and in various steps and arrangements of steps. The drawings are only for the purpose of illustrating preferred embodiments and are not to be construed as limiting the invention.

DETAILED DESCRIPTION OF THE PREFERRED EMBODIMENTS

Figure 1:
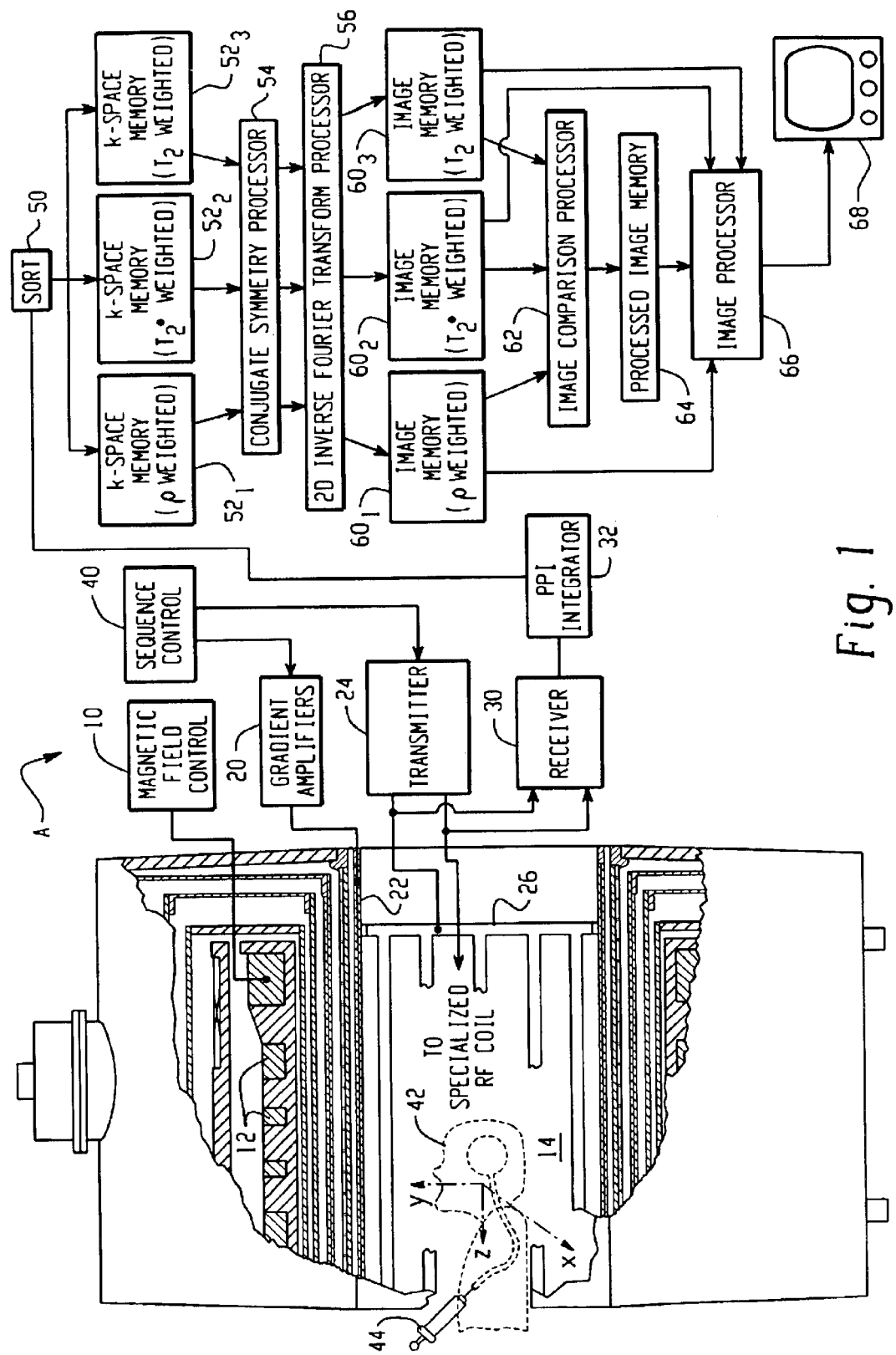
FIG. 1 is a diagrammatic drawing of a magnetic resonance imaging scanner for imaging fluid flow in accordance with one embodiment of the invention.

With reference to FIG. 1, a magnetic resonance imaging (MRI) scanner A includes a main magnetic field control 10 that controls superconducting or resistive magnets 12 such that a substantially uniform, temporally constant main magnetic field $B_0$ is created along a z-axis through an examination region 14. An imaging experiment is conducted by executing a magnetic resonance sequence with the subject being imaged or examined (e.g., patient, phantom, or otherwise) placed at least partially within the examination region 14. The magnetic resonance (MR) sequence includes a series of RF and magnetic field gradient pulses that are applied to the subject to invert or excite magnetic spins, induce magnetic resonance, refocus magnetic resonance, manipulate magnetic resonance, spatially and otherwise encode the magnetic resonance, to saturate spins, and the like.

More specifically, gradient pulse amplifiers 20 apply current pulses to a whole body gradient coil assembly 22 to create magnetic field gradients along x, y and z-axes of the examination region 14. Typically, these include a slice-select magnetic field gradient generator acting in the z-direction to produce the slice-selective ($G_z$) gradient. A phase-select magnetic field gradient generator typically acts in the y-direction to produce the phase-selective ($G_y$) spatial encoding gradient. A frequency-select magnetic field read gradient generator typically acts in the x-direction to produce the frequency-selective ($G_x$) spatial encoding gradient. Of course, the designation of the gradients is preferably user-selectable (e.g., for a particular experiment the y-gradient can be designated as the frequency-selective gradient while the x-gradient can be designated as the phase-selective gradient). Additionally, gradient generators can typically be combined to produce gradients along directions other than the three principle (x, y, z) directions, so that, for example, the slice-selective gradient can be generated along a direction at an acute angle to the z-axis through a combination of generators.

An RF transmitter 24, preferably digital, applies RF pulses or pulse packets to a whole-body RF coil 26 to transmit RF pulses into the examination region. A typical RF pulse is composed of a packet of immediately contiguous pulse segments of short duration which taken together with each other and any applied gradients achieve a selected magnetic resonance manipulation. The RF pulses are used to saturate, excite resonance, invert magnetization, refocus resonance, or manipulate resonance in selected portions of the examination region.

For whole-body applications, the resulting resonance signals, generated as a result of a selected manipulation, are also typically picked up by the whole-body RF coil 26. For imaging limited regions of the subject, local RF coils are commonly placed contiguous to the selected region. For example, as is known in the art, an insertable head coil (not shown) is inserted surrounding a selected brain region at the isocenter of the bore; a selected surface coil (not shown) is employed; or, other such specialized RF coils are employed. In addition to receiving RF pulses, optionally, the local RF coil can also transmit magnetic resonance signals into the selected region.

A phased array receive coil (not shown) can also be used for reading the resonance signals. As is known to those of ordinary skill in the art, a phased array receive coil can be used in conjunction with one of the known partial parallel imaging (PPI) techniques to perform parallel k-space sampling. In these techniques, readout data is obtained in parallel by the component coils of the spatially distributed array, and the spatial information extracted from the combined phased coil array data partially replaces the spatial information ordinarily obtained using gradients. A number of PPI imaging techniques have been developed, including simultaneous acquisition of spatial harmonics (SMASH), sensitivity encoding (SENSE), parallel imaging with localized sensitivities (PILS), et cetera, and these techniques need not be described in detail herein for an enabling disclosure of the invention.

The resultant RF magnetic resonance signals picked up by one or another of the RF coils, or by the phased array receive coil, are employed and demodulated by a receiver 30, preferably digital, to generate a series of data lines. Preferably, a sequence control circuit 40 controls the gradient pulse amplifiers 20 and the RF transmitter 24 to produce an MRI pulse sequence that generates magnetic resonance (MR) signals or echoes received and sampled by the receiver 30. When using partial parallel imaging techniques, a PPI integrator 32 combines the signals from the individual coil components of the phased array (not shown) to obtain k-space samples in parallel according to known PPI techniques, e.g., SMASH, SENSE, PILS, et cetera, that account for the localized coil sensitivities and the spatial location of the component coils of the array.

In one aspect of the invention, the MRI scanner runs a single shot echo planar imaging (SS-EPI) sequence. SS-EPI is a rapid MRI technique which can be used to produce tomographic images, e.g., at video rates, and is particularly useful in perfusion and/or diffusion studies, for functional magnetic resonance imaging (fMRI), et cetera. Preferably, the technique records an entire image in a single $T_R$ period, where $T_R$ represents the repeat time for the SS-EPI sequence.

A patient 42 receives a dose of a magnetic contrast agent 44, such as a gadolinium chelate administered as a bolus injection. This contrast agent-assisted MR imaging is referred to as contrast enhanced imaging. The contrast agent 44 is preferably injected into the bloodstream which transports it through the body of the patient to a region of interest. The contrast agent 44 has distinctive magnetic resonance properties which enable identifiable imaging of the contrast agent 44 as it moves through the patient 42. In the exemplary case the gadolinium chelate reduces the $T_2$ or $T_2^*$ contrast (i.e., darkens the image) in areas where it has penetrated. However, as noted previously, competing factors such as $T_1$ shortening can produce an opposing brightening effect which complicates quantitative analysis of the movement of the contrast agent 44.

In an exemplary imaging experiment, the gadolinium chelate 44 is transported into a region of interest in the brain of the patient 42. The gadolinium chelate is preferably administered to the patient as a bolus injection. The spatial distribution of the concentration of the contrast agent in the brain region as it distributes through the processes of blood flow and perfusion into surrounding tissues is monitored during MR imaging. In this manner, the blood flow through the major blood vessels as well as the perfusion of the blood into the surrounding tissues is studied.

With continuing reference to FIG. 1, the data lines collected by the receiver 30 and optionally processed by the PPI integrator 32 are sorted 50 in accordance with $\rho$, $T_2$, or $T_2^*$ weighting and loaded into corresponding k-space memories $52_1$, $52_2$, $52_3$. For greater speed, data lines are often collected in just over half of k-space. A conjugate symmetry processor 54 calculates conjugately symmetric data lines to complete k-space. A reconstruction processor 56 reconstructs the k-space data into image representations, such as with a two-dimensional inverse Fourier transform or other reconstruction method as is known to the art. The resultant image representations are stored in image memories $60_1$, $60_2$, $60_3$. An image comparing processor 62 combines corresponding resultant images, e.g. forms ratios of the images, to generate flow or perfusion enhanced images which are stored in a processed image memory 64. An image processor 66 converts the contrast enhanced images into appropriate format for display on a monitor 68, such as a CCD display, active matrix monitor, video monitor, or the like.

Figure 2:
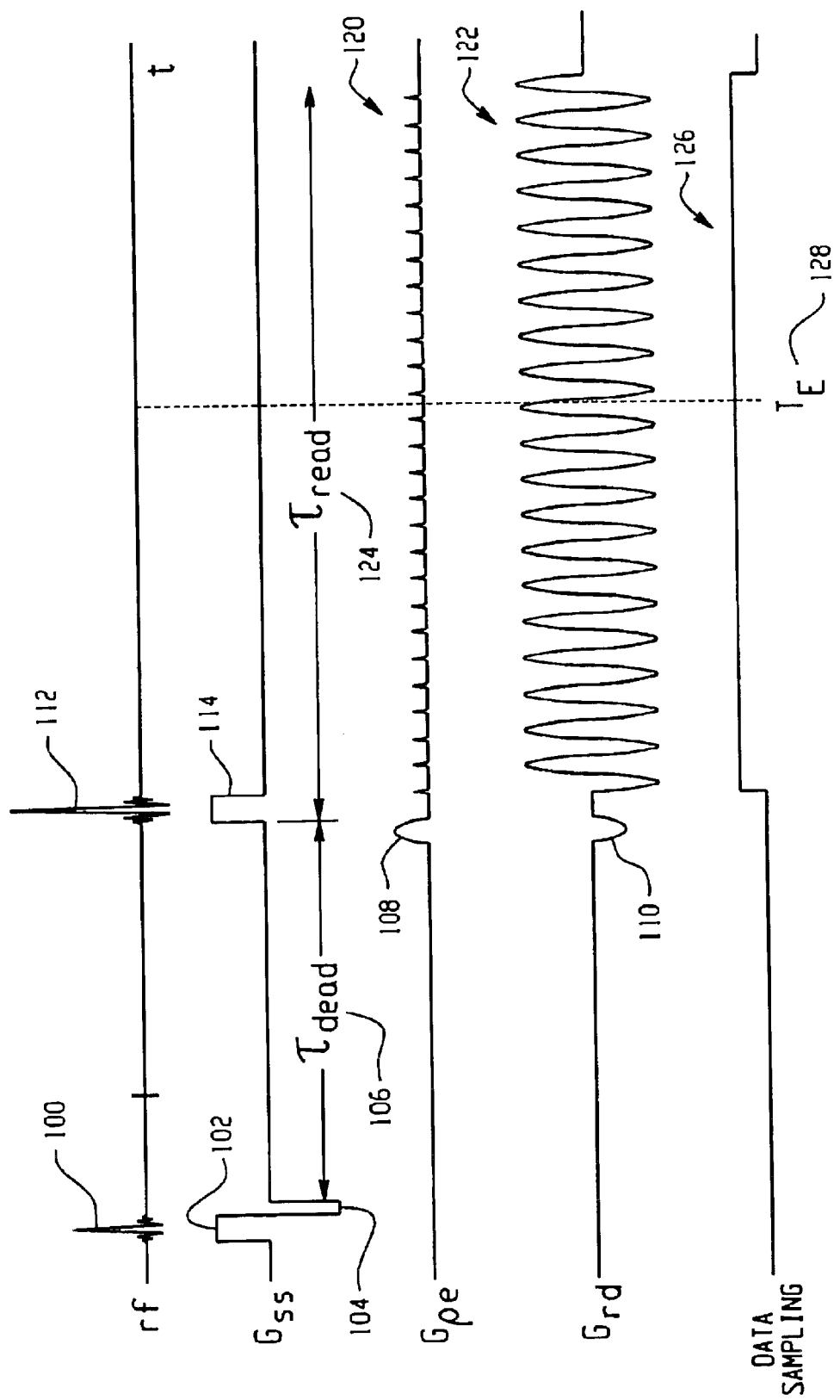
FIG. 2 is a representative qualitative timing diagram for a single-shot echo-planar imaging sequence according to the prior art, which records a $T_2$ weighted image during a single repetition period $T_R$.

With reference now to FIG. 2 along with continued reference to FIG. 1, in a typical SS-EPI timing sequence for recording a $T_2$ weighted image according to the prior art, a 90° RF excitation pulse 100 is applied in conjunction with a slice selective gradient pulse 102 and an opposite polarity rephasing gradient pulse 104 which compensates for dephasing.

After the RF excitation is applied, there is typically a delay period $\tau_{dead}$ 106 whose duration is selected to allow partial $T_2$ relaxation. Thus, the duration of $\tau_{dead}$ 106 is preferably keyed to the $T_2$ behavior of the imaged tissue or contrast agent. Near the end of the delay period $\tau_{dead}$ 106 an initial phase encoding gradient pulse 108 and an initial frequency encoding gradient pulse 110 are applied. A 180° RF inversion pulse 112 is applied in conjunction with a second slice selection gradient pulse 114.

The phase and frequency encoding directions are next cycled so as to traverse k-space and perform the SS-EPI encoding/readout operations. Only a few (about 40) phase and frequency encoding gradient pulses 120 and 122, respectively, are shown in the exemplary qualitative timing sequence of FIG. 2. However, it is to be appreciated that in typical SS-EPI imaging a larger number of pulses are used, for example, 128 or 256 pulses, in order to obtain higher resolution. The SS-EPI encoding and readout timing sequence includes an oscillatory frequency encoding or read gradient 122 which encodes in the readout direction, preferably corresponding to the $k_x$ coordinate in k-space, in a rastering back-and-forth manner. Synchronized with this oscillatory encoding gradient 122 are periodic phase encoding pulses 120 which step through the $k_y$ coordinate in k-space. The phase and frequency encoding combine to spatially encode in-plane positions in the slice. A readout period $\tau_{read}$ 124 is located essentially centered about time-to-echo $T_E$ 128.

It is to be appreciated that the timing sequence of FIG. 2, as well as those of FIGS. 3–6 which follow, are exemplary and qualitative sequences. It will be appreciated by those of ordinary skill in the art that additional pre-pulses (not shown) are optionally added to the sequence shown in FIG. 2, or to any of the forthcoming timing sequences of FIGS. 3–6, to introduce additional contrast such as enhanced $T_1$ weighting, fat suppression, MTC, et cetera. Similarly, a partial parallel imaging (PPI) technique such as SMASH, SENSE, or PILS, is optionally incorporated into any or all of the echo planar readout waveforms discussed herein.

For a $T_2$ weighted image a dead time $\tau_{dead}$ 106 of order 40 msec is typical, corresponding to a time-to-echo $T_E$ 128 of about 80 msec. The SS-EPI readout scan time $\tau_{read}$ 124 is typically of similar magnitude, e.g. less than 300 msec. Thus, the dead time $\tau_{dead}$ 106 is a significant fraction of the total scan time, and the sampling duty cycle for $T_2$ weighted SS-EPI imaging can be as low as 50%.

Figure 3:
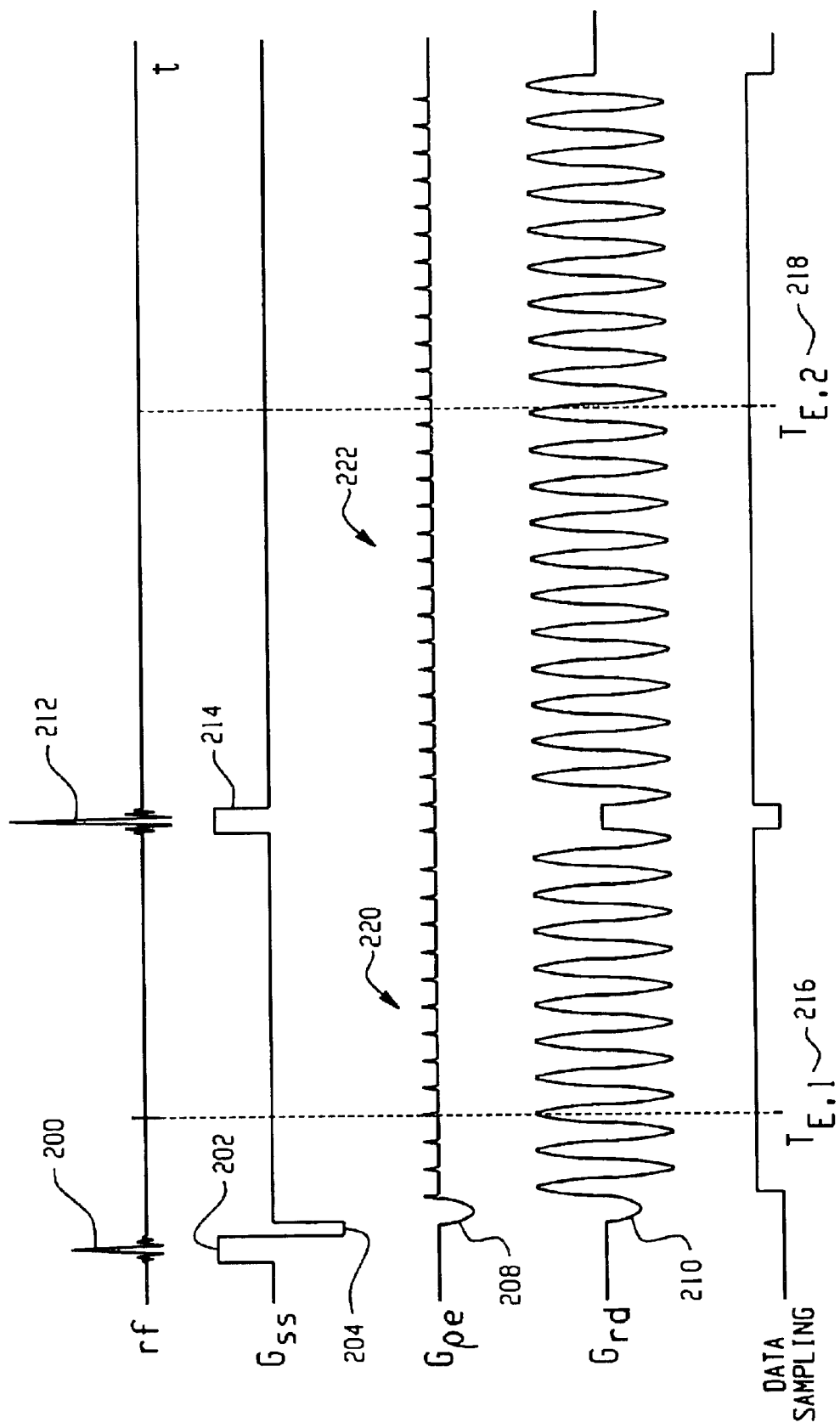
FIG. 3 is a representative qualitative timing diagram for multiple contrast single-shot echo-planar imaging sequence according to one aspect of the invention, wherein a $T_2$ weighted image and a second image, which can be ρ weighted or $T_2^*$ weighted, are recorded during a single repetition period $T_R$.

With reference now to FIG. 3, a timing sequence is shown in accordance with one embodiment of the invention. A $T_2$ weighted image and a second image, which can be $\rho$ weighted or $T_2^*$ weighted, are recorded during a single repetition period $T_R$. The timing sequence includes a 90° RF excitation pulse 200 in conjunction with a slice-select gradient pulse 202 and an opposite polarity rephasing gradient pulse 204 which compensates for dephasing, along with a 180° RF inversion pulse 212 and corresponding slice select gradient 214. The time between the excitation and inversion pulses 200, 212 is filled by a second image recording period. The initial phase encoding gradient pulse 208 and the initial frequency encoding gradient pulse 210 are applied after the RF excitation pulse 200. The first readout begins thereafter. Data lines for a first image are acquired prior to the 180° RF inversion pulse 212, i.e. during the corresponding dead time $\tau_{dead}$ 106 of FIG. 2. The phase encoding gradients are applied such that data acquired around a time $T_{E,1}$ 216 is at the center of k-space. Depending upon the timing of the first time-to-echo $T_{E,1}$ 216, this first image is relatively $\rho$ weighted or $T_2^*$ weighted. The 180° RF excitation pulse 212 is then applied in conjunction with the slice selection gradient pulse 214 and the second, $T_2$ weighted image is acquired about a time-to-echo $T_{E,2}$ 218 which is preferably centered on the spin-echo induced by the inversion pulse 212.

In recording the two images, it will be appreciated that the phase stepping of the first image uses phase-select gradient pulses 220 with the same polarity as the phase stepping pulses of the second image 222. However, because the 180° RF pulse 212 reverses the accumulated phase of the resonance spins, the k-space is effectively re-traversed in the same $k_y$ direction for the two images.

Once again, it is to be appreciated that the timing sequence of FIG. 3, as well as those of FIGS. 2 and FIGS. 4–6, are exemplary and qualitative sequences. Pre-pulses can be optionally included to introduce additional contrast such as enhanced $T_1$ weighting, fat suppression, MTC, et cetera. Partial parallel imaging (PPI) techniques can also optionally be incorporated into the readout of the first image, the second image, or both images, using known techniques such as SMASH, SENSE, PILS, et cetera.

The timing sequence of FIG. 3 provides additional image data over the prior art contrast enhanced imaging methods for the same imaging time. The additional data can be used, for example, to compensate for non-$T_2$ components of the $T_2$ weighted image. Such correction can be done by comparing the two images in a $T_{2-T2}^*$ analysis or a $T_2$-$\rho$ analysis. In this manner, a more purely $T_2$ weighted image can be obtained, thereby facilitating accurate quantitative analysis of the perfusion of the gadolinium chelate 44 (FIG. 1). It is to be appreciated that the method illustrated in FIGS. 1 and 3 overcome the prior art time constraint limitations on the collection of such additional data during the dynamic perfusion process by advantageously using the dead time in the prior art $T_2$ weighted SS-EPI timing sequence (FIG. 2) to record the additional data.

Figure 4:
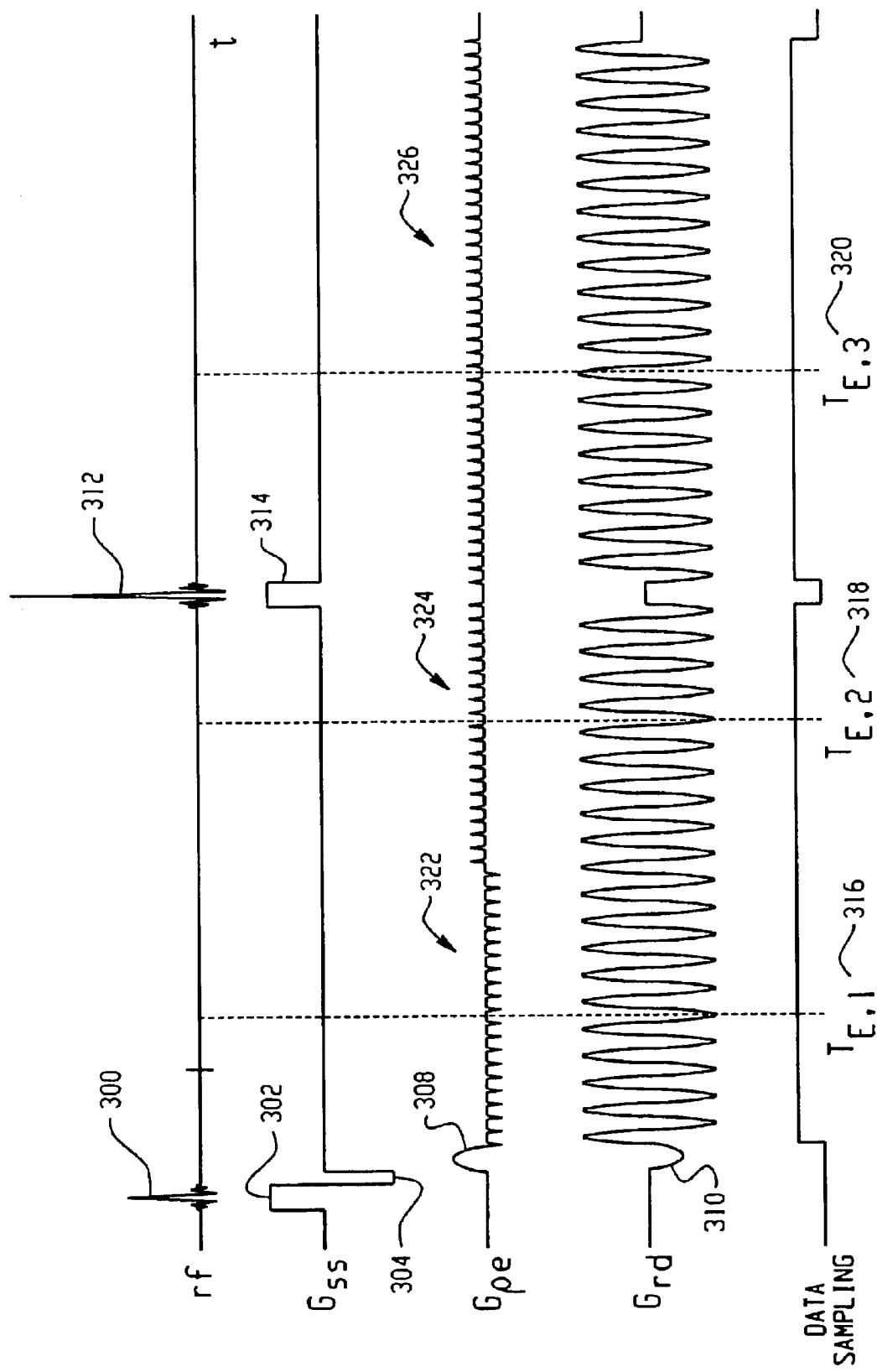
FIG. 4 is a representative qualitative timing diagram for a multiple contrast single-shot echo-planar imaging sequence according to another aspect of the invention, wherein three images with ρ, $T_2^*$ and $T_2$ weighting are recorded during a single repetition period $T_R$.

With reference now to FIG. 4 along with continuing reference to FIG. 1, a timing sequence is described that generates data lines for $\rho$, $T_2^*$ and $T_2$ images during a single repetition period $T_R$. The timing sequence of FIG. 4 is similar to that of FIG. 3, including an initial RF excitation pulse 300 with a corresponding slice-select gradient pulses 302, 304, similarly positioned initial phase encoding gradient pulse 308 and the initial frequency encoding gradient pulse 310. The time is preferably lengthened between application of the excitation pulse 300 and a 180° RF inversion pulse 312 with a corresponding slice selection gradient pulse 314. Data lines centered at $T_{E,1}$ 316 are sorted 50 into the $\rho$ weighted k-space memory $52_1$. Data lines centered at $T_{E,2}$ 318 are sorted 50 into the $T_2^*$ weighted k-space memory $52_2$. Data lines centered at $T_{E,3}$ 320 are sorted 50 into the $T_2$ weighted k-space memory $52_3$.

In the timing sequence of FIG. 4, it will be observed that the phase stepping of the $\rho$ weighted image uses phase-select gradient pulses 322 of opposite polarity and equal magnitude and number compared with phase stepping gradient pulses 324 of the $T_1^*$ weighted image. Thus, the same central portion of k-space is traversed in opposite $k_y$ directions for the two images. Phase encode gradients 326 step the data lines back through the central region of k-space with the data line at time $T_{E,3}$ at the center of k-space. Data lines sampled after the 180° pulse remote from $T_{E,3}$ and phase encoded near an edge of k-space are optionally also sorted into the $T_2^*$ or $\rho$ weighted k-space. In this manner, the data lines away from the center of k-space are shared by two or by all three images.

Once again, it is to be appreciated that the qualitative timing sequence of FIG. 4 can optionally include additional elements known to the art that produce additional contrast such as enhanced $T_1$ weighting, fat suppression, MTC, et cetera. Incorporation of partial parallel imaging (PPI) techniques into one or more of the image readouts can advantageously reduce the readout time and subsequently the overall imaging time.

Figure 5:
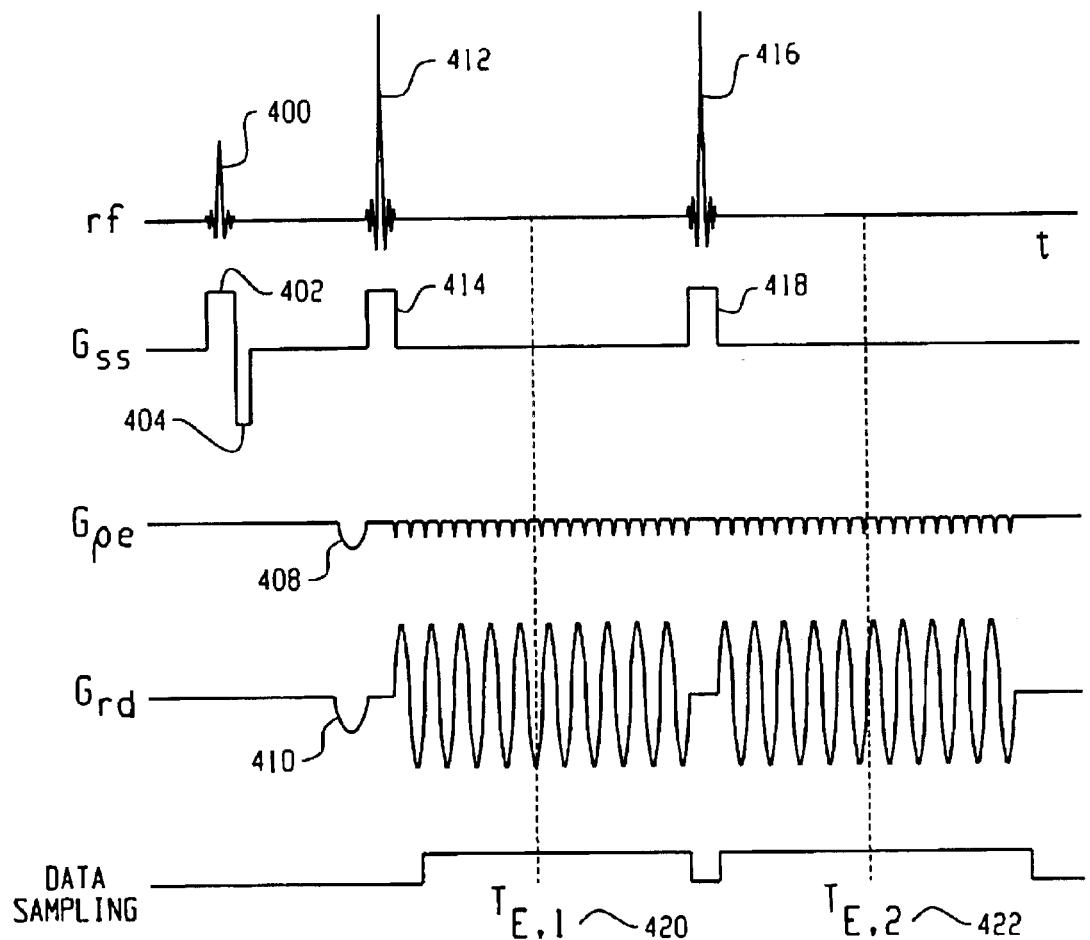
FIG. 5 is a representative qualitative timing diagram for a multiple contrast echo-planar imaging sequence according to yet another aspect of the invention, in which data usable for the generation of two $T_2$ weighted images are collected during each single repetition period $T_R$.

With reference now to FIG. 5, in another embodiment, two $T_2$ weighted images are recorded during a single repetition period $T_R$. This sequence is applicable to single shot $T_2$ mapping. An RF excitation pulse 400 is applied with a corresponding slice select pulse 402, 404. An inversion pulse 412 and a corresponding slice selection gradient pulse 414 induce a first spin-echo. Data lines for a first $T_2$ weighted image corresponding to a time-to-echo $T_{E,1}$ 420 are sampled. Subsequently, a second 180° inversion pulse 416 with a corresponding slice selection gradient pulse 418 is applied to induce a second spin-echo. Data lines for a second $T_2$ weighted image corresponding to a time-to-echo $T_{E,2}$ 422 are then sampled during read gradient pulses of a second EPI segment. Of course, additional cycles each including a 180° inversion pulse and oscillating read gradient pulses can be appended to the sequence, constrained by the length of the time constant $T_2$.

The timing sequences shown in FIGS. 3–5 preferably generate a full set of k-space data in a single $T_R$, i.e. single-shot EPI (SS-EPI). The speed of the SS-EPI technique permits, for example, real-time perfusion studies with corrected $T_2$ weighted image data. Of course, data can also be collected over several $T_R$.

Figure 6:
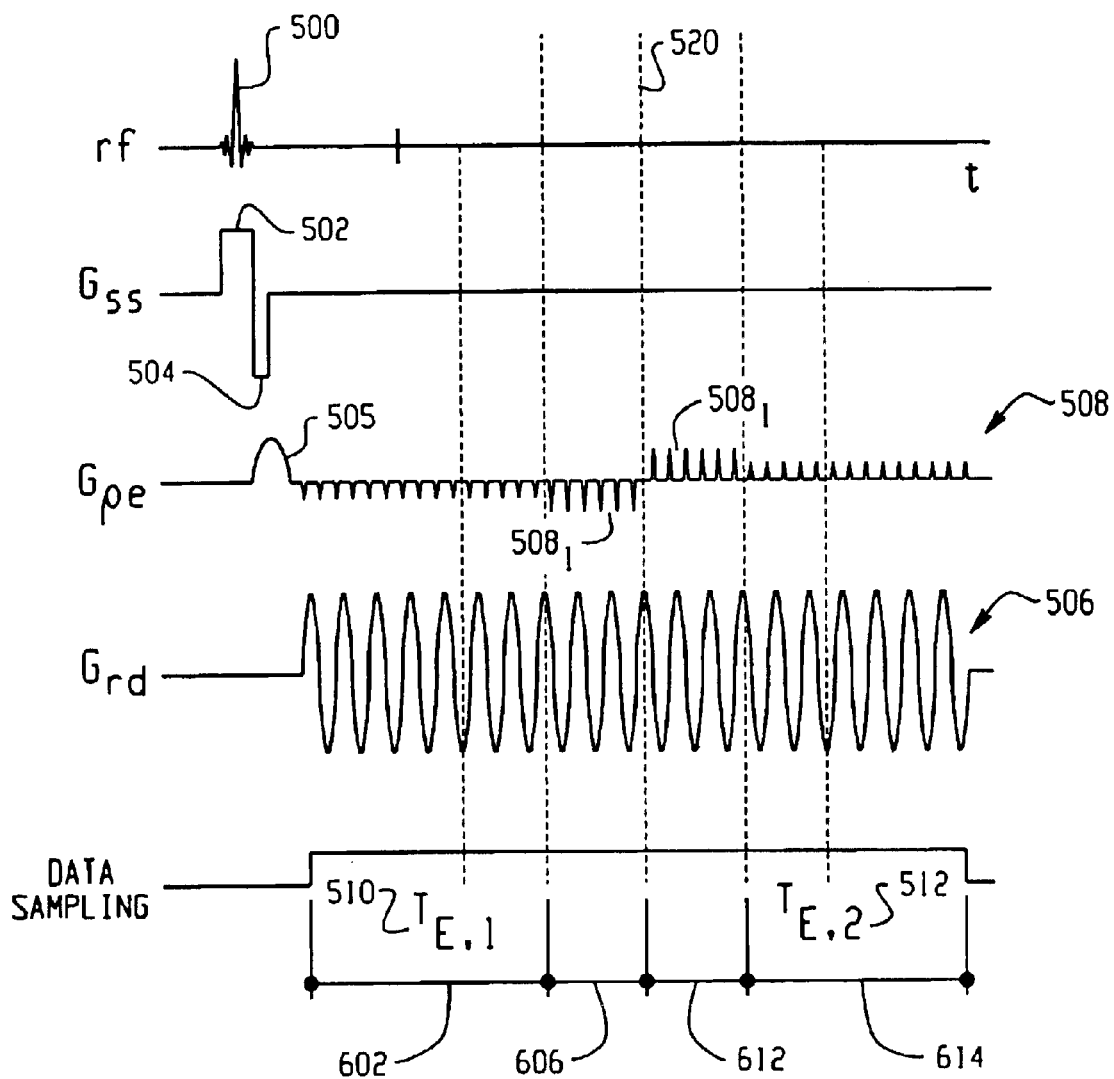
FIG. 6 is a representative qualitative timing diagram for a multiple field echo imaging sequence according to still yet another aspect of the invention.

With reference now to FIG. 6, in yet another embodiment, two $T_2^*$ weighted images are generated in a single acquisition period. Such a sequence is applicable, for example, to single shot $T_2^*$ mapping, or to fat/water separation imaging.

An RF excitation pulse 500 is applied with a corresponding slice select gradient 502, 504 to induce resonance in a selected slice. An initial phase gradient pulse 505 preferably positions the magnetization out of the center of k-space in the phase encode direction.

An oscillating read gradient 506 induces a string of field echoes, each of which is sampled to generate one data line of k-space. Phase encode gradients 508 applied before each data line is sampled step the data lines through k-space. These data lines, which are temporally centered at $T_{E,1}$ 510 are reconstructed into an image with predominant ρ density weighting. The polarity of the phase encode gradient pulses 508 is reversed 520 and the data lines are stepped back through k-space. The data collected prior to the phase encode gradient rewind is more purely proton density weighted and those after the phase encode gradient reversal are more heavily $T_2^*$ weighted. Images reconstructed from the data sets centered on $T_{E,1}$ 510 and $T_{E,2}$ 512 are combined by the processor 64 to emphasize $T_2^*$ weighting effects and remove the effects of proton density weighting.

Figure 7:
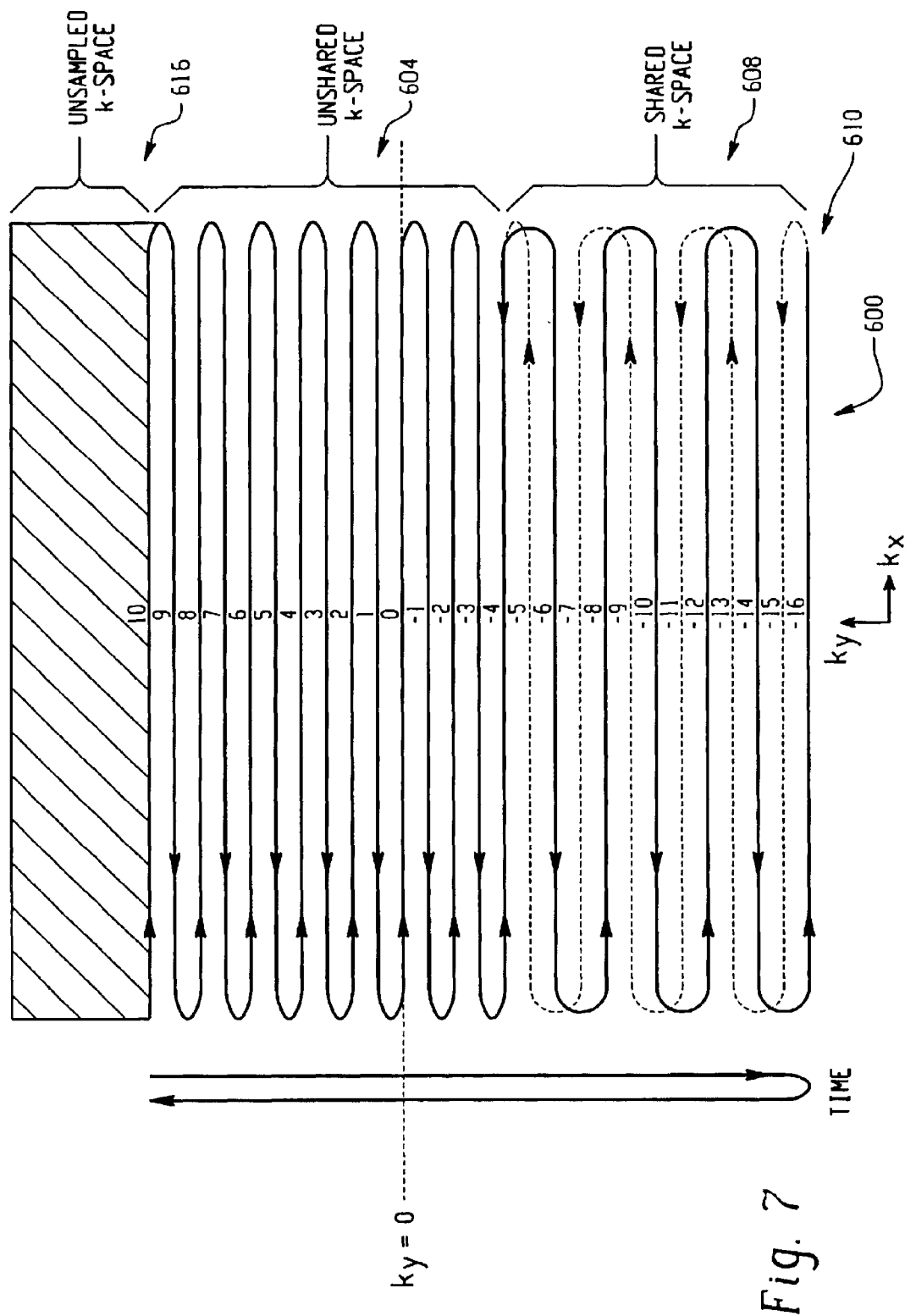
FIG. 7 is a representative diagrammatic representation of the traversal of k-space with EPI data showing data sharing between images near an extremity of k-space during a multiple-contrast SS-EPI slice measurement.

With continuing reference to FIG. 6 and with further reference now to FIG. 7, some data lines are shared by the two images. FIG. 7 shows the sampling of k-space 600 during the EPI multiple echo data acquisition whose timing diagram is shown in FIG. 6. The collection along the $k_x$ direction rasters back-and-forth. Before each forward or backward pass a phase encode pulse 508 is applied to step the acquisition in the $k_y$ direction. In a data acquisition portion 602 around $T_{E,1}$ that corresponds to an unshared k-space region 604, this $k_y$ stepping occurs in single-steps. This data is sorted into the ρ weighted k-space memory $52_1$.

A second data acquisition portion 606 is phase encoded in a shared, peripheral k-space region 608. Here, the $k_y$ stepping occurs in double-steps through the application of higher strength phase encoding pulses $508_1$. As the acquisition continues in the $-k_y$ direction, the odd $k_y$ values (−5, −7, . . . −15) are skipped and only the even $k_y$ values (−6, −8, . . . −16) are acquired. At a $-k_y$ edge 610 of k-space 600 the phase select pulse polarity reverses 520 and k-space is traversed in the $+k_y$ direction. The data obtained from the second portion 606 are stored in both the ρ weighted k-space memory $52_1$ and the $T_2^*$ weighted k-space memory $52_2$, i.e. the data is shared.

A third data portion 612 is acquired in the shared k-space region 608, with the acquisition now proceeding in the $+k_y$ direction. The odd $k_y$ values are now acquired in the $+k_y$ direction (−15, −13, . . . −5). The third data portion 612 is again recorded in both the ρ weighted k-space memory $52_1$, and the $T_2^*$ weighted k-space memory $52_2$.

Echoes in a fourth data portion 614 around $T_{E,2}$ are phase encoded in single steps near the center of k-space, i.e. in the k-space region 604. The data lines from the sequence portion 614 are sorted into the centered, unshared region of the $T_2^*$ k-space memory $52_2$.

An unsampled region 616 of k-space is filled by data lines that are conjugately symmetric to data lines in the shared k-space region 608.

Data sharing can advantageously be combined with optional pre-pulses and other sequence elements known to the art that produce additional contrast such as enhanced $T_1$ weighting, fat suppression, MTC, et cetera.

Incorporation of partial parallel imaging (PPI) techniques along with data sharing for one or more of the image readouts can further reduce imaging time.

In one preferred embodiment, the method improves upon the prior art by providing for acquisition of data in addition to the usual SS-EPI $T_2$ weighted scan. The additional data is used to generate more purely $T_2$ weighted data. A second scan ($T_2^*$ or ρ weighted) is acquired and is quantitatively compared with the $T_2$ weighted scan to produce a third image which has a purer $T_2$ weighted contrast. For example, a $T_2$-$T_2$ or a $T_2$-ρ analysis is preferably performed. The multiple echo SS-EPI is preferably used in conjunction with a contrast-enhanced imaging experiment, such as a dynamic perfusion experiment using a gadolinium chelate contrast agent that reduces the $T_2$ contrast. Of course, other contrast agents can also be used in accordance with the method. Based upon the improved $T_2$ contrast of the third image which is calculated from the first and second measured images, a quantitative determination of the perfusion of the contrast agent is obtained. This perfusion determination can be obtained by taking ratios or logarithms of the two images in the image comparison processor 62 to quantify the time course and arrival curves. Given a predetermined relationship between the contrast agent concentration and the reduction in $T_2$ contrast (e.g., an empirical relationship), the concentration distribution of the contrast agent is determined with respect to spatial and temporal coordinates. Thus, for example, the perfusion of the gadolinium chelate are quantitatively determined based upon the third image.

In another embodiment, a temporal evolution of a first clinical parameter is obtained from a temporal series of images obtained using a first echo planar readout waveform. A temporal evolution of a second clinical parameter is obtained from a temporal series of images obtained using a second echo planar readout waveform, the first and second readout waveforms being included in a single multiple-contrast EPI imaging sequence. The temporal evolution of the first and second clinical parameters are combined, e.g. mathematically or by qualitative interpretation by medical personnel, to obtain additional diagnostic information that is unavailable from prior art methods. Alternatively, the images obtained from the first and second readout waveforms are combined to form a third image, and the temporal evolution of a parameter related to the third image is then extracted.

In yet another embodiment, a first scan of a multiple echo enhanced contrast SS-EPI experiment provides a high contrast image which is responsive to low concentrations of the contrast agent, but which is effectively overexposed in regions of high concentration such as the major blood vessels. A second image reconstructed from the sequence preferably is a medium contrast image which clearly shows the contrast agent in the major vessels but does not resolve the lower concentration perfusion areas as well as the first image. The two images together provide a medical doctor with more complete information than is provided by either image by itself. The contrast agent is again preferably a gadolinium chelate, although of course other contrast agents can also be used in accordance with the method.

In still yet another embodiment, a first image of a multiple-echo enhanced-contrast SS-EPI experiment is tuned to be highly sensitive to the contrast agent. In the exemplary case of a gadolinium chelate contrast agent, this first image is preferably a $T_2$ weighted image. A second image of the sequence is preferably recorded under conditions which are not sensitive to the contrast agent. For the gadolinium chelate, a $\rho$ weighted image is appropriate. In this way, the first image of the contrast agent is placed into context by the second image, which serves as a reference image. The images are both acquired during a single repetition period $T_R$, so that subsequent registry is unnecessary. Additionally, any movement of the patient during the dynamic perfusion experiment is automatically included in both the contrast enhanced images and the reference images.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A method of magnetic resonance imaging comprising:
   (a) administering a magnetic resonance contrast agent to a subject which contrast agent alters $T_1$, $T_2$ and $T_2^*$ magnetic resonance characteristics;
   (b) exciting magnetic resonance in a region of interest of the subject which receives the contrast agent;
   (c) applying a first echo planar readout waveform during the excited resonance and generating a plurality of data lines of first image data;
   (d) applying a second echo planar readout waveform during the excited resonance after the first echo planar readout waveform and generating a plurality of lines of $T_2$ or $T_2^*$ weighted image data;
   (e) reconstructing the image data to generate a first image representation and a $T_2$ or $T_2^*$ weighted image representation; and
   (f) correcting the $T_2$ or $T_2^*$ weighted image representation with the first image representation.

2. The method as set forth in claim 1, further including:
   applying a third echo planar readout waveform and generating the other of $T_2$ and $T_2^*$ weighted image data.

3. The method as set forth in claim 2, further including:
   applying an RF inversion pulse between the second and third echo planar readout waveforms, such that the second echo planar readout waveform generates $T_2^*$ weighted data and the third echo planar readout waveform generates $T_2$ weighted data.

4. The method as set forth in claim 3, further including:
   reconstructing the $T_2$ weighted data into a $T_2$ weighted image representation; and
   modifying the $T_2$ weighted image representation with the first image representation.

5. The method as set forth in claim 1, further including:
   repeating steps (b)–(f) a plurality of times to generate a series of first image representations and a series of $T_2$ or $T_2^*$ weighted image representations; and
   combining the series of first image representations and the series of $T_2$ or $T_2^*$ weighted image representations to generate a third series depicting a temporal evolution of the contrast agent in the region of interest.

6. The method as set forth in claim 1, further including:
   (g) combining the first image representation and the $T_2$ or $T_2^*$ weighted image representation to generate a third image representation; and repeating steps (b)–(g) a plurality of times to generate a series of third image representations depicting a temporal evolution of the contrast agent in the region of interest.

7. The method as set forth in claim 1, wherein the contrast agent includes a gadolinium chelate.

8. The imaging method according to claim 1, wherein:
   in the step of reconstructing the $T_2$ or $T_2^*$ weighted image representation, a portion of the encoded and read resonance from the first echo planar readout waveform is reconstructed into the $T_2$ or $T_2^*$ weighted image representation.

9. The imaging method according to claim 1, wherein:
   the first echo planar readout waveform phase encoding includes,
     phase encoding a first portion of the resonance such that a $k_y$ component single-steps in a first direction, and
     phase encoding a second portion of the resonance such that the $k_y$ component double-steps in the first direction;
   the second echo planar readout waveform phase encoding includes,
     phase encoding a first portion of the resonance such that the $k_y$ component double-steps opposite to the first direction, and
     phase encoding a second portion of the resonance such that the $k_y$ component single-steps opposite to the first direction; and
   the reconstructing step includes,
     reconstructing the first and second portions of the first echo planar readout waveform and the first portion of the second echo planar readout waveform into the first image representation, and
     reconstructing the second portion of the first echo planar readout waveform and the first and second portions of the second echo planar readout waveform into the second image representation.

10. A method of magnetic resonance imaging comprising:
    administering a contrast agent to a subject which alters $T_1$ and $T_2$ magnetic resonance characteristics;
    exciting magnetic resonance in a region of interest of the subject which receives the contrast agent;
    applying a first echo planar readout waveform during the excited resonance and generating first image data having $T_1$ contrast;
    applying a refocusing RF inversion pulse after the first echo planar readout waveform;
    applying a second echo planar readout waveform after the refocusing RF inversion pulse and generating second image data having $T_2$ contrast and some $T_1$ contrast;
    reconstructing the first image data into a first reconstructed image having $T_1$ contrast;
    reconstructing the second image data into a second reconstructed image having both $T_1$ and $T_2$ contrast; and
    correcting the second reconstructed image based on the first reconstructed image to reduce the $T_1$ contrast of the second reconstructed image.

11. A method of magnetic resonance imaging comprising:
    (a) administering a magnetic resonance contrast agent to a subject which contrast agent alters $T_1$, $T_2$ and $T_2^*$ magnetic resonance characteristics;
    (b) exciting magnetic resonance in a region of interest of the subject which receives the contrast agent;
    (c) applying a first echo planar readout waveform and generating first image data;

(d) applying a second echo planar readout waveform and generating $T_2$ or $T_2^*$ weighted image data;

(e) reconstructing (i) the $T_2$ or $T_2^*$ weighted image data and (ii) a portion of the first image data temporally adjacent to the $T_2$ or $T_2^*$ weighted image data to generate a $T_2$ or $T_2^*$ weighted image representation;

(f) reconstructing (i) a portion of the $T_2$ or $T_2^*$ weighted image data temporally adjacent to the first image data and (ii) the first image data to generate a first image representation; and (g) correcting the $T_2$ or $T_2^*$ weighted image representation with the first image representation.

12. The method as set forth in claim 11, wherein the portion of the $T_2$ or $T_2^*$ weighted readout waveform temporally adjacent to the first image data and the portion of the first image data temporally adjacent to the $T_2$ or $T_2^*$ weighted image data include interleaved data lines adjacent an edge of k-space.

13. The method as set forth in claim 12, further including:
generating additional data lines by conjugate symmetry.

14. A method of magnetic resonance imaging comprising:
(a) administering a magnetic resonance contrast agent to a subject which alters $T_1$, $T_2$ and $T_2^*$ magnetic resonance characteristics;

(b) exciting magnetic resonance in a region of interest of the subject which receives the contrast agent, the exciting including applying a radio frequency excitation pulse and subsequently applying a refocusing inversion pulse;

(c) during a deadtime between the radio frequency excitation pulse and the refocusing pulse, applying a first echo planar readout waveform and generating first image data;

(d) after the applying of the refocusing pulse, applying a second echo planar readout waveform and generating $T_2$ weighted second image data;

(e) reconstructing the image data to generate a first image representation and a $T_2$ weighted image representation; and (f) correcting the $T_2$ weighted image representation with the first image representation.

15. A method of contrast enhanced magnetic resonance imaging in which a subject is injected with a contrast agent that alters $T_1$ and $T_2$ decay characteristics, magnetic resonance is excited in a region of interest, the excited magnetic resonance is permitted to decay for a preselected duration to optimize one of $T_2$ and $T_2^*$ weighting, and after the preselected duration an echo planar sequence is applied to generate $T_2$ or $T_2^*$ weighted data, which $T_2$ or $T_2^*$ weighted data is most strongly affected by the effect of the contrast agent on $T_2$ decay and is secondarily affected by the effect of the contrast agent on $T_1$ decay which continues after the preselected duration, the method further including:

during the preselected duration, applying another echo planar sequence to generate $T_1$ weighted data; and using the $T_1$ weighted data to correct the $T_2$ or $T_2^*$ weighted data for the effect of the continuing $T_1$ decay to generate a $T_2$ or $T_2^*$ image that is corrected for the effect of the contrast agent on $T_1$ decay.

16. A magnetic resonance imaging apparatus comprising:
a main magnet which generates a temporally constant magnetic field through an examination region;

an RF system which excites and manipulates magnetic resonance in the examination region and which receives and demodulates magnetic resonance signals from the examination region into data lines;

a sorter which sorts the data lines between a first data memory and a second data memory;

a gradient magnetic field system which generates magnetic field gradients across the examination region to spatially encode the resonance signals;

a sequence controller which,
(i) controls the RF system to induce resonance including spin refocusing using an inversion RF pulse;
(ii) controls the RF and gradient systems to implement a first echo planar readout waveform during a deadtime preceding the inversion RF pulse which generates non-$T_2$ weighted data lines;
(iii) controls the RF and gradient systems to implement a second echo planar readout waveform after the inversion RF pulse which generates $T_2$ data lines, and
(iv) controls the sorter to sort the non-$T_2$ and $T_2$ weighted data lines between the first and second data memories; and a reconstruction processor which reconstructs data lines from the first data memory into a first image representation and data lines from the second data memory into a second image representation.

17. The magnetic resonance apparatus as set forth in claim 16 wherein:
the sequence controller controls the sorter to sort
(i) all of the non-$T_2$ weighted data lines and a portion of the $T_2$ weighted data lines into the first image memory and
(ii) all of the $T_2$ weighted data lines and a portion of the non-$T_2$ weighted data lines into the second image memory.

18. The magnetic resonance apparatus as set forth in claim 16 wherein the RF system further includes:
a phased array receive coil; and
a partial parallel imaging (PPI) integrator which processes the readout of the phased array receive coil to generate data lines.

19. The magnetic resonance apparatus as set forth in claim 18 wherein the partial parallel imaging (PPI) integrator processes the readout of the phased array receive coil using one of a simultaneous acquisition of spatial harmonics (SMASH) technique, a sensitivity encoding (SENSE) technique, and a parallel imaging with localized sensitivities (PILS) technique.

* * * * *